US009371310B2

(12) United States Patent
Yang et al.

(10) Patent No.: US 9,371,310 B2
(45) Date of Patent: *Jun. 21, 2016

(54) PROCESS FOR THE PREPARATION OF 3-(3-CHLORO-1*H*-PYRAZOL-1-YL)PYRIDINE

(71) Applicant: Dow AgroSciences LLC, Indianapolis, IN (US)

(72) Inventors: Qiang Yang, Zionsville, IN (US); Beth Lorsbach, Indianapolis, IN (US); Carl DeAmicis, Indinanapolis, IN (US); Ann M. Buysse, Carmel, IN (US); Ronald Ross, Jr., Zionsville, IN (US); Xiaoyong Li, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/666,822

(22) Filed: Mar. 24, 2015

(65) Prior Publication Data

US 2016/0031849 A1  Feb. 4, 2016

Related U.S. Application Data

(63) Continuation of application No. 14/517,357, filed on Oct. 17, 2014, now Pat. No. 9,029,556.

(60) Provisional application No. 62/031,557, filed on Jul. 31, 2014.

(51) Int. Cl.
*C07D 401/04* (2006.01)

(52) U.S. Cl.
CPC .................... *C07D 401/04* (2013.01)

(58) Field of Classification Search
CPC .................................................. C07D 401/04
USPC ....................................................... 546/275.4
See application file for complete search history.

(56) References Cited

U.S. PATENT DOCUMENTS

| 3,597,341 | A | 8/1971 | Oswald |
| 4,080,457 | A | 3/1978 | Harrison et al. |
| 4,260,765 | A | 4/1981 | Harrison et al. |
| 4,407,803 | A | 10/1983 | Haviv et al. |
| 4,536,506 | A | 8/1985 | Marcoux et al. |
| 4,824,953 | A | 4/1989 | Bronn |
| 5,220,028 | A | 6/1993 | Iwasawa et al. |
| 5,625,074 | A | 4/1997 | Daum et al. |
| 5,631,380 | A | 5/1997 | Haas et al. |
| 5,652,372 | A | 7/1997 | Muller et al. |
| 5,693,657 | A | 12/1997 | Lee et al. |
| 5,750,718 | A | 5/1998 | Muller et al. |
| 5,817,677 | A | 10/1998 | Linz et al. |
| 5,854,264 | A | 12/1998 | Anthony et al. |
| 5,854,265 | A | 12/1998 | Anthony et al. |
| 5,869,681 | A | 2/1999 | Muller et al. |
| 6,040,331 | A | 3/2000 | Yamamoto et al. |
| 6,218,418 | B1 | 4/2001 | Pevarello et al. |
| 6,506,747 | B1 | 1/2003 | Betageri et al. |
| 6,548,525 | B2 | 4/2003 | Galemmo, Jr. et al. |
| 6,720,427 | B2 | 4/2004 | Sanner et al. |
| 6,878,196 | B2 | 4/2005 | Harada et al. |
| 6,916,927 | B2 | 7/2005 | Bunnage et al. |
| 6,965,032 | B2 | 11/2005 | Freudenberger et al. |
| 7,192,906 | B2 | 3/2007 | Hirohara et al. |
| 7,196,104 | B2 | 3/2007 | Askew, Jr. et al. |
| 7,319,108 | B2 | 1/2008 | Schwink et al. |
| 7,774,978 | B2 | 8/2010 | Ding et al. |
| 7,803,832 | B2 | 9/2010 | Critcher et al. |
| 7,910,606 | B2 | 3/2011 | Nazare et al. |
| 7,923,573 | B2 | 4/2011 | Tamaki et al. |
| 8,163,756 | B2 | 4/2012 | Flynn et al. |
| 8,222,280 | B2 | 7/2012 | Liu et al. |
| 8,901,153 | B2 | 12/2014 | Buysse et al. |
| 9,029,556 | B1 * | 5/2015 | Yang et al. ................. 546/275.4 |
| 2002/0013326 | A1 | 1/2002 | Tiebes et al. |
| 2003/0153464 | A1 | 8/2003 | Nakamura et al. |
| 2003/0213405 | A1 | 11/2003 | Harada et al. |
| 2004/0043904 | A1 | 3/2004 | Yamaguchi et al. |
| 2004/0082629 | A1 | 4/2004 | Iwataki et al. |
| 2005/0038059 | A1 | 2/2005 | Mueller et al. |
| 2005/0176710 | A1 | 8/2005 | Schwink et al. |
| 2006/0135778 | A1 | 6/2006 | Schnatterer et al. |
| 2006/0160857 | A1 | 7/2006 | Buettelmann et al. |
| 2006/0160875 | A1 | 7/2006 | Gaines et al. |

(Continued)

FOREIGN PATENT DOCUMENTS

| EP | 0097323 | 1/1984 |
| EP | 0190457 | 8/1986 |

(Continued)

OTHER PUBLICATIONS

Kempe et al., "Responsive Glyco-poly(2-oxaoline)s: Synthesis, Cloud Point Tuning, and Lectin Binding," Biomacromolecules 2011, vol. 12, pp. 2591-2600.
Fields et al., "Preparation of Trifluoromethyl-Pyrazoles and -Pyrazolines by the Reaction of 2,2,2-Trifluorodiazoethane with Carbon-Carbon Multiple Bonds," Journal of Fluorine Chemistry, 1979, vol. 13, pp. 147-158.
Bradbury et al., "Enzyme-catalysed peptide amidation," Eur. J. Biochem. 1987, vol. 169, pp. 579-584.
International Search Report and Written Opinion for PCT/US2014/061005 mailed Dec. 16, 2014.
International Search Report and Written Opinion for PCT/US2014/061006 mailed Dec. 8, 2014.
International Search Report and Written Opinion for PCT/US2014/061007 mailed Dec. 31, 2014.
International Search Report and Written Opinion for PCT/US2014/061009 mailed Dec. 8, 2014.
International Search Report and Written Opinion for PCT/US2014/061010 mailed Dec. 15, 2014.
International Search Report and Written Opinion for PCT/US2014/061012 mailed Dec. 15, 2014.

(Continued)

*Primary Examiner* — Patricia L Morris
(74) *Attorney, Agent, or Firm* — Carl D. Corvin; Barnes & Thornburg LLP

(57) ABSTRACT

3-(3-Chloro-1H-pyrazol-1-yl)pyridine is prepared by coupling 3-bromopyridine with commercially available 3-aminopyrazole, purifying the 3-(3-amino-1H-pyrazol-1-yl)pyridine by crystallization, and converting the amino group to a chloro group by a Sandmeyer reaction.

9 Claims, No Drawings

(56) References Cited

U.S. PATENT DOCUMENTS

| | | |
|---|---|---|
| 2006/0167020 A1 | 7/2006 | Dickerson et al. |
| 2006/0287365 A1 | 12/2006 | Billen et al. |
| 2006/0287541 A1 | 12/2006 | Nishino et al. |
| 2007/0049604 A1 | 3/2007 | Nam et al. |
| 2007/0167426 A1 | 7/2007 | Siddiqui et al. |
| 2008/0004301 A1 | 1/2008 | Tamaki et al. |
| 2008/0027046 A1 | 1/2008 | Annan et al. |
| 2009/0023709 A1 | 1/2009 | Gillespie et al. |
| 2009/0069288 A1 | 3/2009 | Breinlinger et al. |
| 2009/0137524 A1 | 5/2009 | Billen et al. |
| 2009/0325956 A1 | 12/2009 | Taniguchi et al. |
| 2010/0130474 A1 | 5/2010 | Bothmann et al. |
| 2010/0204164 A1 | 8/2010 | Crouse et al. |
| 2010/0286169 A1 | 11/2010 | Guiles et al. |
| 2010/0292253 A1 | 11/2010 | Trullinger et al. |
| 2010/0305200 A1 | 12/2010 | Velicelebi et al. |
| 2011/0021771 A1 | 1/2011 | Mallais et al. |
| 2011/0048261 A1 | 3/2011 | Shimura |
| 2011/0098287 A1 | 4/2011 | Bretschneider et al. |
| 2011/0118290 A1 | 5/2011 | Bretschneider et al. |
| 2011/0166129 A1 | 7/2011 | Machacek et al. |
| 2011/0166143 A1 | 7/2011 | Bretschneider et al. |
| 2011/0184188 A1 | 7/2011 | Wada et al. |
| 2011/0201649 A1 | 8/2011 | Matsuzaki et al. |
| 2011/0212949 A1 | 9/2011 | Bretschneider et al. |
| 2011/0275583 A1 | 11/2011 | Bretschneider et al. |
| 2011/0319428 A1 | 12/2011 | Fublein et al. |
| 2012/0053146 A1 | 3/2012 | Parker et al. |
| 2012/0094837 A1 | 4/2012 | Muhlthau et al. |
| 2012/0095023 A1 | 4/2012 | Bretschneider et al. |
| 2012/0110701 A1 | 5/2012 | Garizi et al. |
| 2012/0110702 A1 | 5/2012 | Yap et al. |
| 2012/0115811 A1 | 5/2012 | Du et al. |
| 2012/0165345 A1 | 6/2012 | Bretschneider et al. |
| 2012/0172218 A1 | 7/2012 | Crouse et al. |
| 2012/0220453 A1 | 8/2012 | Lowe et al. |
| 2012/0252770 A1 | 10/2012 | Berger et al. |
| 2013/0072382 A1 | 3/2013 | Trullinger et al. |
| 2013/0089622 A1 | 4/2013 | Trullinger et al. |
| 2013/0109566 A1 | 5/2013 | Niyaz et al. |
| 2013/0261141 A1 | 10/2013 | Bretschneider et al. |
| 2013/0288893 A1 | 10/2013 | Buysse et al. |
| 2013/0291227 A1 | 10/2013 | Buysse et al. |
| 2013/0324736 A1 | 12/2013 | Ross, Jr. et al. |
| 2013/0324737 A1 | 12/2013 | Ross, Jr. et al. |

FOREIGN PATENT DOCUMENTS

| | | |
|---|---|---|
| EP | 0205024 | 12/1986 |
| EP | 0248315 | 12/1987 |
| EP | 0425948 | 5/1991 |
| EP | 1273582 | 1/2003 |
| EP | 1321463 | 6/2003 |
| EP | 1329160 | 7/2003 |
| JP | 1987-153273 | 7/1987 |
| JP | 1988-174905 | 7/1988 |
| JP | 1989-226815 | 9/1989 |
| JP | 2003-212864 | 7/2003 |
| JP | 2004-051628 | 2/2004 |
| JP | 2004-292703 | 10/2004 |
| JP | 2012-188418 | 10/2012 |
| JP | 2013-075871 | 4/2013 |
| JP | 2013-082699 | 5/2013 |
| JP | 2013-082704 | 5/2013 |
| JP | 2013-107867 | 6/2013 |
| JP | 2013-129651 | 7/2013 |
| JP | 2013-129653 | 7/2013 |
| WO | 94/13644 | 6/1994 |
| WO | 97/36897 | 10/1997 |
| WO | 98/49166 | 11/1998 |
| WO | 00/35919 | 6/2000 |
| WO | 01/34127 | 5/2001 |
| WO | 01/90078 | 11/2001 |
| WO | 02/083111 | 10/2002 |
| WO | 03/008405 | 1/2003 |
| WO | 03/072102 | 9/2003 |
| WO | 2004/041813 | 5/2004 |
| WO | 2005/070925 | 8/2005 |
| WO | 2005/074875 | 8/2005 |
| WO | 2006/023462 | 3/2006 |
| WO | 2006/033005 | 3/2006 |
| WO | 2006/046593 | 5/2006 |
| WO | 2006/103045 | 10/2006 |
| WO | 2007/005838 | 1/2007 |
| WO | 2007/087427 | 8/2007 |
| WO | 2007/098826 | 9/2007 |
| WO | 2008/005457 | 1/2008 |
| WO | 2008/079277 | 7/2008 |
| WO | 2008/090382 | 7/2008 |
| WO | 2009/149858 | 12/2009 |
| WO | 2010/006713 | 1/2010 |
| WO | 2010/009290 | 1/2010 |
| WO | 2010/012442 | 2/2010 |
| WO | 2010/033360 | 3/2010 |
| WO | 2010/048207 | 4/2010 |
| WO | 2010/060379 | 6/2010 |
| WO | 2010/075376 | 7/2010 |
| WO | 2010/129497 | 11/2010 |
| WO | 2010/133336 | 11/2010 |
| WO | 2010/146236 | 12/2010 |
| WO | 2011/003065 | 1/2011 |
| WO | 2011/043371 | 4/2011 |
| WO | 2011/045224 | 4/2011 |
| WO | 2011/045240 | 4/2011 |
| WO | 2011/091153 | 7/2011 |
| WO | 2011/101229 | 8/2011 |
| WO | 2011/126903 | 10/2011 |
| WO | 2011/128304 | 10/2011 |
| WO | 2011/134964 | 11/2011 |
| WO | 2011/138285 | 11/2011 |
| WO | 2011/163518 | 12/2011 |
| WO | 2012/000896 | 1/2012 |
| WO | 2012/004217 | 1/2012 |
| WO | 2012/007500 | 1/2012 |
| WO | 2012035011 | 3/2012 |
| WO | 2012/052412 | 4/2012 |
| WO | 2012/061290 | 5/2012 |
| WO | 2012/070114 | 5/2012 |
| WO | 2012/102387 | 8/2012 |
| WO | 2012/108511 | 8/2012 |
| WO | 2012/147107 | 11/2012 |
| WO | 2012/168361 | 12/2012 |
| WO | 2013/000931 | 1/2013 |
| WO | 2013/010946 | 1/2013 |
| WO | 2013/010947 | 1/2013 |
| WO | 2013/062980 | 5/2013 |
| WO | 2013/064324 | 5/2013 |
| WO | 2013/156431 | 10/2013 |
| WO | 2013/156433 | 10/2013 |

OTHER PUBLICATIONS

International Search Report and Written Opinion for PCT/US2014/061014 mailed Dec. 15, 2014.
International Search Report and Written Opinion for PCT/US2014/061016 mailed Dec. 15, 2014.
International Search Report and Written Opinion for PCT/US2014/061022 mailed Dec. 29, 2014.
International Search Report and Written Opinion for PCT/US2014/061023 mailed Dec. 15, 2014.
International Search Report and Written Opinion for PCT/US2014/061024 mailed Dec. 15, 2014.
International Search Report and Written Opinion for PCT/US2014/061027 mailed Dec. 15, 2014.
International Search Report and Written Opinion for PCT/US2014/061029 mailed Dec. 15, 2014.
International Search Report and Written Opinion for PCT/US2014/061030 mailed Dec. 15, 2014.
International Search Report and Written Opinion for PCT/US2013/029615 mailed May 8, 2013.

* cited by examiner

PROCESS FOR THE PREPARATION OF 3-(3-CHLORO-1H-PYRAZOL-1-YL)PYRIDINE

CROSS REFERENCE TO RELATED APPLICATIONS

This application is a continuation of U.S. application Ser. No. 14/517,357 filed on Oct. 17, 2014, which claims the benefit of the following U.S. Provisional Patent Application Ser. No. 62/031,557 filed Jul. 31, 2014, the entire disclosures of which are hereby expressly incorporated by reference in this Application.

BACKGROUND

The present invention concerns an improved process for preparing 3-(3-chloro-1H-pyrazol-1-yl)pyridine.

US 20130288893(A1) describes, inter alia, certain (3-halo-1-(pyridin-3-yl)-1H-pyrazol-4-yl)amides and carbamates and their use as pesticides. The route to prepare such compounds involved the preparation of 3-(3-chloro-1H-pyrazol-1-yl)pyridine by the direct coupling of 3-bromopyridine with 3-chloropyrazole. The 3-chloropyrazole was prepared by a) treating 1H-pyrazole with 2-dimethylsulfamoyl chloride and sodium hydride to provide N,N-dimethyl-1H-pyrazole-1-sulfonamide, b) treating the N,N-dimethyl-1H-pyrazole-1-sulfonamide with perchloroethane and n-butyl lithium to provide 3-chloro-N,N-dimethyl-1H-pyrazole-1-sulfonamide, and c) removing the N,N-dimethylsulfonamide from 3-chloro-N,N-dimethyl-1H-pyrazole-1-sulfonamide with trifluoroacetic acid to give the 3-chloropyrazole.

The disclosed process produces low yields, relies on a starting material that is difficult to prepare (3-chloropyrazole) and provides a product that is difficult to isolate in a pure form. It would be desirable to have a process for preparing 3-(3-chloro-1H-pyrazol-1-yl)pyridine (5b) that avoids these problems.

SUMMARY

The present invention provides such an alternative by coupling 3-bromopyridine with commercially available 3-aminopyrazole, purifying the 3-(3-amino-1H-pyrazol-1-yl)pyridine (8a) by crystallization, and converting the amino group to a chloro group by a Sandmeyer reaction. Thus, the present invention concerns a process for preparing 3-(3-chloro-1H-pyrazol-1-yl)pyridine (5b),

(5b)

which comprises
a) treating 3-bromopyridine

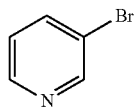

with 3-aminopyrazole

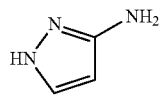

in a water-miscible polar aprotic organic solvent at a temperature of about 75° C. to about 155° C. in the presence of a catalytic amount of copper(I) chloride and a base to provide 3-(3-amino-1H-pyrazol-1-yl)pyridine (8a)

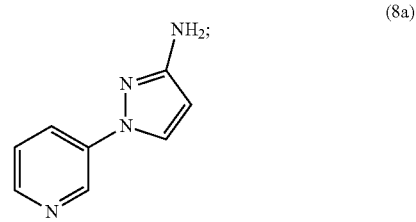 [SMILES: Nc1ccn(-c2cccnc2)n1]

(8a)

b) crystallizing the 3-(3-amino-1H-pyrazol-1-yl)pyridine (8a) from water;
c) treating the 3-(3-amino-1H-pyrazol-1-yl)pyridine (8a) in aqueous hydrochloric acid with sodium nitrite at a temperature of about 0° C. to about 25° C. to provide the diazonium salt (8b)

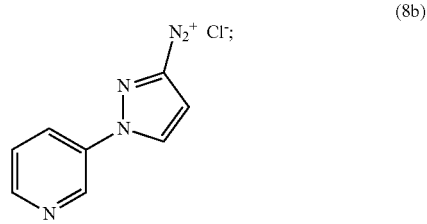

(8b)

and
d) treating the diazonium salt (8b) with copper chloride at a temperature of about 0° C. to about 25° C.

DETAILED DESCRIPTION

The present invention provides an improved process for preparing 3-(3-chloro-1H-pyrazol-1-yl)pyridine (5b) by coupling 3-bromopyridine with commercially available 3-aminopyrazole, purifying the 3-(3-amino-1H-pyrazol-1-yl)pyridine (8a) by crystallization, and converting the amino group to a chloro group by a Sandmeyer reaction.

In the first step, 3-bromopyridine is coupled with 3-aminopyrazole in a water-miscible polar aprotic organic solvent at a temperature of about 75° C. to about 155° C. in the presence of a catalytic amount of copper chloride and a base to provide 3-(3-amino-1H-pyrazol-1-yl)pyridine (8a). While stoichiometric amounts of 3-bromopyridine and 3-aminopyrazole are required, it is often convenient to use an excess of 3-aminopyrazole. An excess from about 10 mole percent to about 50 mole percent 3-aminopyrazole is preferred. The coupling is run in the presence of about 5 mole percent to about 50 mole percent copper chloride, preferably from about 15 mole percent to about 30 mole percent copper chloride. The copper chloride may be either copper(I) chloride or copper(II) chloride. The coupling is also run in the presence of a base. While stoichiometric amounts of 3-bromopyridine and base are required, it is often convenient to use about a 1.5 fold to about a 2 fold excess of base. Alkali metal carbonates are preferred bases. The coupling is performed in a water-miscible polar aprotic organic solvent. Polar aprotic organic solvents that are soluble in water include nitriles such as acetonitrile, sulfoxides such as dimethyl sulfoxide, and amides such as N-methylpyrrolidinone, N,N-dimethylformamide, and N,N-dimethylacetamide. N,N-Dimethylformamide is particularly preferred.

In a typical reaction, copper(I) chloride, 3-aminopyrazole, potassium carbonate and N,N-dimethylformamide are introduced into a reaction vessel under a nitrogen atmosphere and 3-bromopyridine is gradually added. The mixture is heated at about 110° C. until most of the 3-bromopyridine has reacted. The mixture is allowed to cool and most of the solvent is removed under reduced pressure. The crude 3-(3-amino-1H-pyrazol-1-yl)pyridine (8a) is conveniently isolated and purified by crystallization from water.

The purified 3-(3-amino-1H-pyrazol-1-yl)pyridine (8a) is then converted to the desired 3-(3-chloro-1H-pyrazol-1-yl)pyridine (5b) by treatment in aqueous hydrochloric acid with sodium nitrite at a temperature of about 0° C. to about 25° C. to provide a diazonium salt followed by treatment of the diazonium salt with copper chloride at a temperature of about 0° C. to about 25° C. While stoichiometric amounts of reagents are required, it is often convenient to use an excesses of reagents with respect to the 3-(3-amino-1H-pyrazol-1-yl)pyridine (8a). Thus, aqueous hydrochloric acid is used in large excess as the reaction medium. Sodium nitrite is used in about a 1.5 fold to about a 2 fold excess. Copper chloride is used in about 5 mole percent to about 50 mole percent excess, preferably from about 15 mole percent to about 30 mole percent excess. The copper chloride may be either copper(I) chloride, copper(II) chloride or copper powder. To suppress foaming during the reaction a water-immiscible organic solvent such as toluene or chloroform can be added during the treatment of the diazonium salt with copper chloride.

In a typical reaction, a mixture of 3-(3-amino-1H-pyrazol-1-yl)pyridine (8a) and aqueous hydrochloric acid are mixed and cooled to about 0° C. An aqueous solution of sodium nitrite is slowly added maintaining the temperature below about 5° C. The suspension is stirred at about 0° C. for about 2 hours. In a separate vessel, a mixture of copper(I) chloride and toluene are cooled to about 0° C. and the chilled suspension of diazonium salt is added at a rate maintaining the temperature below about 5° C. The mixture is allowed to warm to about ambient temperature. After completion of the reaction, the mixture is treated with aqueous sodium hydroxide to adjust the pH to about 8 to about 10. The resulting solution is extracted with a water-immiscible organic solvent. After removal of the solvent, the 3-(3-chloro-1H-pyrazol-1-yl)pyridine (5b) can be used directly in the next step, or further purified by standard techniques such as flash column chromatography or crystallization.

The following examples are presented to illustrate the invention.

EXAMPLES

1. Preparation of
3-(3-amino-1H-pyrazol-1-yl)pyridine (8a)

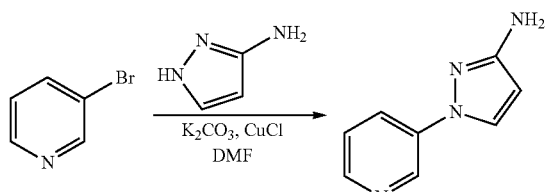

A 4-neck round bottomed flask (500 mL) was charged with copper(I) chloride (2.51 g, 25.3 mmol), 1H-pyrazol-3-amine (15.8 g, 190 mmol), potassium carbonate (35.0 g, 253 mmol), and N,N-dimethylformamide (100 mL). The mixture was stirred under nitrogen for 10 minutes and 3-bromopyridine (12.2 mL, 127 mmol) was added. The mixture was heated at 110° C. for 18 hours, at which point HPLC analysis indicated that ~15.5% 3-bromopyridine remained. The reaction was allowed to cool to 20° C. and concentrated to give a brown residue. Water (200 mL) was added and the resulting suspension was stirred at 20° C. for 2 hours and filtered. The solid was rinsed with water (2×50 mL) and dried to afford a pale green solid. The solid was suspended in water (200 mL) and the resulting suspension was heated at 90° C. for 2 hours and was filtered hot through a Celite® pad. The pad was rinsed with hot water (50 mL). The combined filtrates were allowed to cool to 20° C. to afford a yellow suspension, which was stirred at 20° C. for 2 hours and filtered. The solid was rinsed with water (2×50 mL) and air dried to afford the desired product as a light yellow crystalline solid (11.6 g, 57%): mp 169-172° C.; $^1$H NMR (400 MHz, DMSO-$d_6$) δ 9.07-8.82 (m, 1H), 8.33 (dd, J=4.6, 1.5 Hz, 1H), 8.24 (d, J=2.6 Hz, 1H), 8.00 (ddd, J=8.4, 2.7, 1.4 Hz, 1H), 7.42 (ddd, J=8.5, 4.6, 0.8 Hz, 1H), 5.80 (d, J=2.6 Hz, 1H), 5.21 (s, 2H); $^{13}$C NMR (101 MHz, DMSO-$d_6$) δ 157.67, 144.68, 138.00, 136.22, 128.30, 123.95, 123.17, 97.08; ESIMS m/z 161 ([M+H]$^+$).

2. Preparation of
3-(3-chloro-1H-pyrazol-1-yl)pyridine (5b)

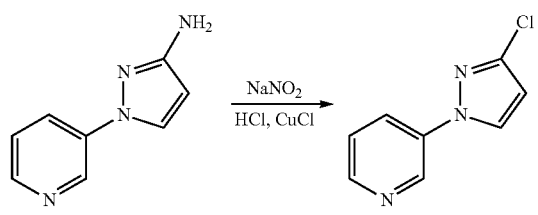

To a 3-neck round bottomed flask (100 mL) was charged 3-(3-amino-1H-pyrazol-1-yl)pyridine (0.500 g, 3.12 mmol) and hydrochloric acid (37 wt %, 3 mL). The mixture was cooled to 0° C. and a solution of sodium nitrite (0.431 g, 6.24 mmol) in water (3 mL) was added in portions at <5° C. The resulting yellow suspension was stirred at 0° C. for 2 hours. To a separate 3-neck round bottomed flask (100 mL) was charged copper(I) chloride (0.371 g, 3.75 mmol) and toluene (3 mL). It was cooled to 0° C. and the yellow suspension was added in portions at <5° C. The resulting mixture was allowed to warm to 20° C. and stirred for 18 hours. It was basified with 50% sodium hydroxide to pH 10 and extracted with ethyl acetate (2×20 mL). The organic layers were concentrated to dryness and the residue was purified by flash column chromatography using 0-10% ethyl acetate/hexanes as eluent. The fractions containing the desired product were concentrated to give the title compound as a white solid (0.340 g, 61%): mp 104-106° C.; $^1$H NMR (400 MHz, CDCl$_3$) δ 8.93 (d, J=27 Hz, 1H), 8.57 (dd, J=4.8, 1.4 Hz, 1H), 8.02 (ddd, J=8.3, 2.7, 1.5 Hz, 1H), 7.91 (d, J=2.6 Hz, 1H), 7.47-7.34 (M, 1H), 6.45 (d, J=2.6 Hz, 1H); $^{13}$C NMR (101 MHz, CDCl$_3$) δ 148.01, 142.72, 140.12, 135.99, 128.64, 126.41, 124.01, 108.08; EIMS m/z 179 ([M]$^+$).

What is claimed is:

1. A process for preparing 3-(3-chloro-1H-pyrazol-1-yl)pyridine (5b)

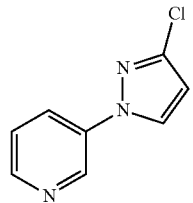
(5b)

which comprises
a) treating 3-bromopyridine

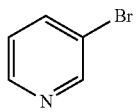

with 3-aminopyrazole in an excess of about 10 mole percent to about 50 mole percent

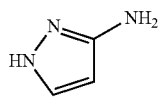

in a water-miscible polar aprotic organic solvent at a temperature of about 75° C. to about 155° C. in the presence of about 5 mole percent to about 30 mole percent of copper chloride and a base in an excess of about 1.5 fold to about 2 fold to provide 3-(3-amino-1H-pyrazol-1-yl)pyridine (8a)

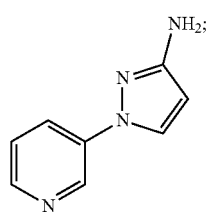
(8a)

b) crystallizing the 3-(3-amino-1H-pyrazol-1-yl)pyridine (8a) from water;
c) treating the 3-(3-amino-1H-pyrazol-1-yl)pyridine (8a) in excess aqueous hydrochloric acid with sodium nitrite in an excess of about 1.5 fold to about 2 fold at a temperature of about 0° C. to about 25° C. to provide the diazonium salt (8b)

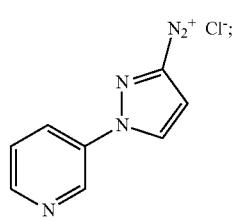
(8b)

and
d) treating the diazonium salt (8b) with about 5 mole percent to about 50 mole percent copper chloride at a temperature of about 0° C. to about 25° C.

2. The process of claim 1, wherein the water-miscible polar aprotic organic solvent is acetonitrile, dimethyl sulfoxide, N-methylpyrrolidinone, N,N-dimethylformamide or N,N-dimethylacetamide.

3. The process of claim 2, wherein the water-miscible polar aprotic organic solvent is N,N-dimethylacetamide.

4. The process of claim 1, wherein a water immiscible organic solvent is added in step d) to suppress foaming.

5. The process of claim 1, wherein the copper chloride is copper (I) chloride.

6. The process of claim 1, wherein the copper chloride is copper (II) chloride.

7. The process of claim 1, wherein the copper chloride in step (d) is in an amount of from about 15 mole percent to 30 mole percent.

8. The process of claim 4, wherein the water immiscible organic solvent is toluene or chloroform.

9. A process for preparing 3-(3-chloro-1H-pyrazol-1-yl)pyridine (5b)

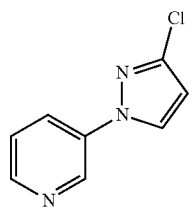
(5b)

which comprises
a) treating 3-bromopyridine

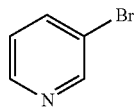

with 3-aminopyrazole

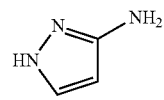

in N,N-dimethylformamide at a temperature of about 110° C. in the presence of about 5 mole percent to about 30 mole percent of copper (I) chloride and an excess of potassium carbonate to provide 3-(3-amino-1H-pyrazol-1-yl)pyridine (8a)

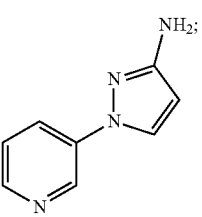
(8a)

b) crystallizing the 3-(3-amino-1H-pyrazol-1-yl)pyridine (8a) from water;
c) treating the 3-(3-amino-1H-pyrazol-1-yl)pyridine (8a) in excess aqueous hydrochloric acid with sodium nitrite in an excess of about 1.5 fold to about 2 fold at a temperature of about 0° C. to about 5° C. to provide the diazonium salt (8b)
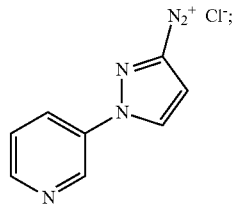
(8b)
and
d) treating the diazonium salt (8b) with copper (I) chloride at a temperature of about 0° C. to about 25° C.
* * * * *